United States Patent [19]

Bonello et al.

[11] Patent Number: 4,798,598
[45] Date of Patent: * Jan. 17, 1989

[54] GUIDE FOR A CATHETER

[75] Inventors: Philippe Bonello, Geneva; Maurice Jeanmonod, Meyrin, both of Switzerland

[73] Assignee: Sarcem S.A., Meyrin, Switzerland

[*] Notice: The portion of the term of this patent subsequent to Mar. 22, 2005 has been disclaimed.

[21] Appl. No.: 42,651

[22] Filed: Apr. 28, 1987

[30] Foreign Application Priority Data

May 23, 1986 [CH] Switzerland .......................... 2083/86
Jan. 28, 1987 [CH] Switzerland ............................ 289/87

[51] Int. Cl.$^4$ ............................................. A61M 21/00
[52] U.S. Cl. ..................................... 604/280; 604/95; 128/772; 128/658
[58] Field of Search ............... 128/772, 656, 657, 658, 128/348.1; 604/95, 170, 264, 280

[56] References Cited

U.S. PATENT DOCUMENTS

| | | |
|---|---|---|
| 3,528,406 | 9/1970 | Jeckel et al. |
| 3,612,058 | 10/1971 | Ackerman ............................... 604/95 |
| 3,973,556 | 8/1976 | Fleischhacker ..................... 267/180 |
| 4,215,703 | 8/1980 | Willson . |
| 4,456,017 | 6/1984 | Miles . |
| 4,534,363 | 8/1985 | Gold . |
| 4,538,622 | 9/1985 | Simson et al. ....................... 128/772 |
| 4,543,090 | 9/1985 | McCoy . |
| 4,548,206 | 10/1985 | Osborne ............................... 128/772 |
| 4,554,929 | 11/1985 | Samson et al. ..................... 128/772 |
| 4,732,163 | 3/1988 | Bonello et al. ...................... 128/772 |

FOREIGN PATENT DOCUMENTS f2130885 6/1984 United Kingdom .

Primary Examiner—C. Fred Rosenbaum
Assistant Examiner—Colleen Reilly
Attorney, Agent, or Firm—Young & Thompson

[57] ABSTRACT

A catheter guide which comprises a head (3) formed by a coil spring (4) presenting a central zone (6) where the coils of this spring are spaced, the free end of this head (3) being obturated. A tubular element (2) connects this head to a control housing (1) to which it is fixed in a removable way. A control device (14,15) of the bending of the head (3) comprises a control member (14) sliding in the housing (1) connected by a traction member (15) to an excentered point on the free end of the head (3). A cutting device (17 to 21) of the traction member (15) is located in the housing (1). The tubular element (2) is constituted by a coil spring (4) having abutting coils covered by a tight coating (9) in plastic material.

9 Claims, 3 Drawing Sheets

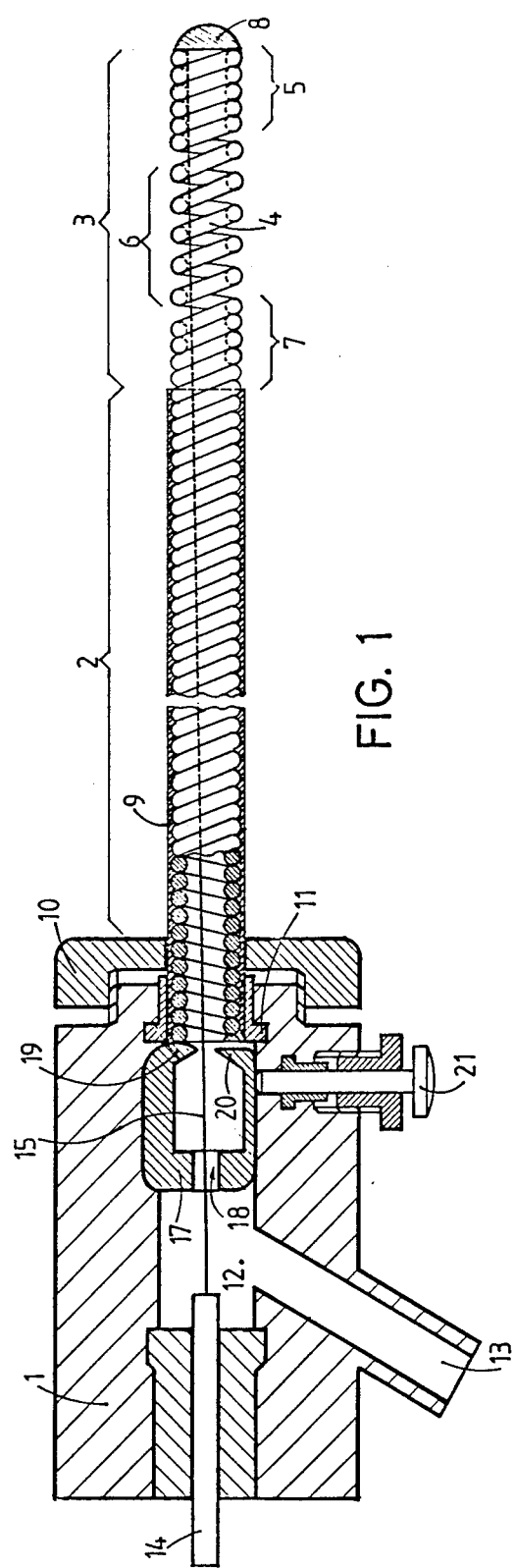
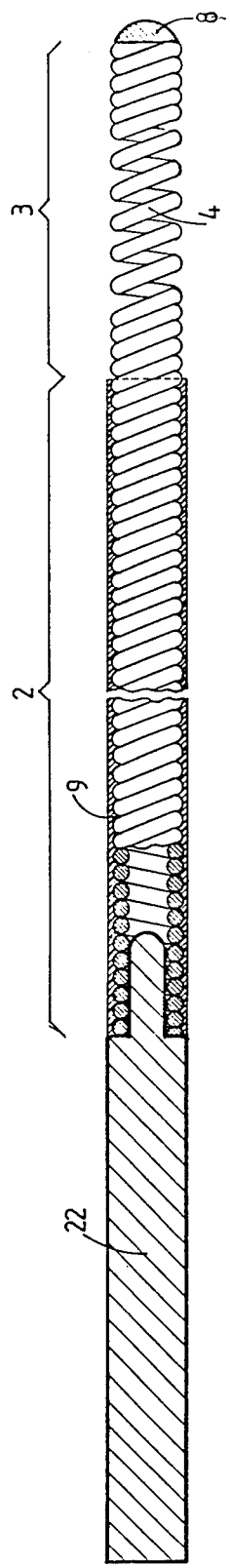

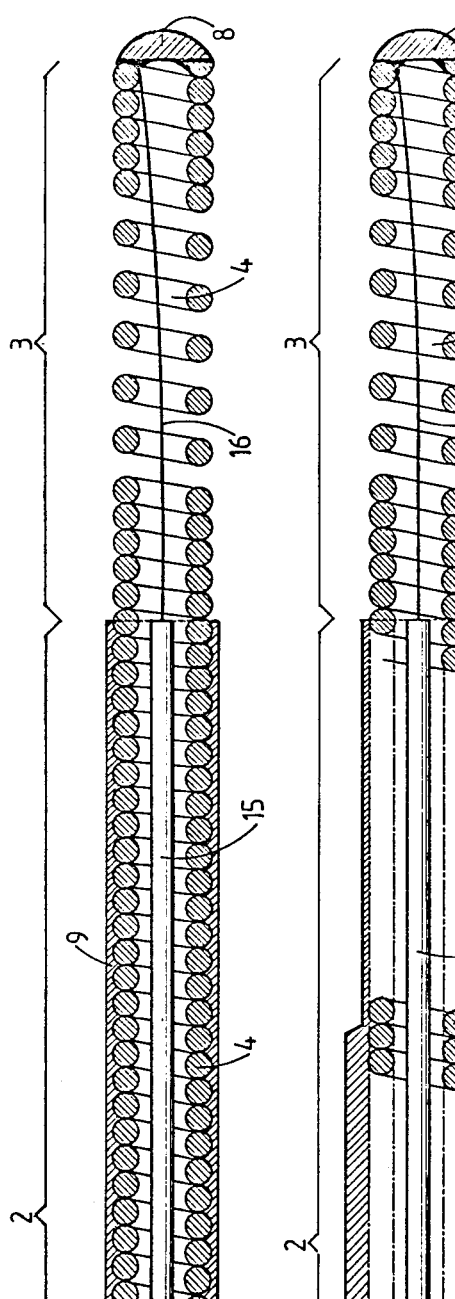
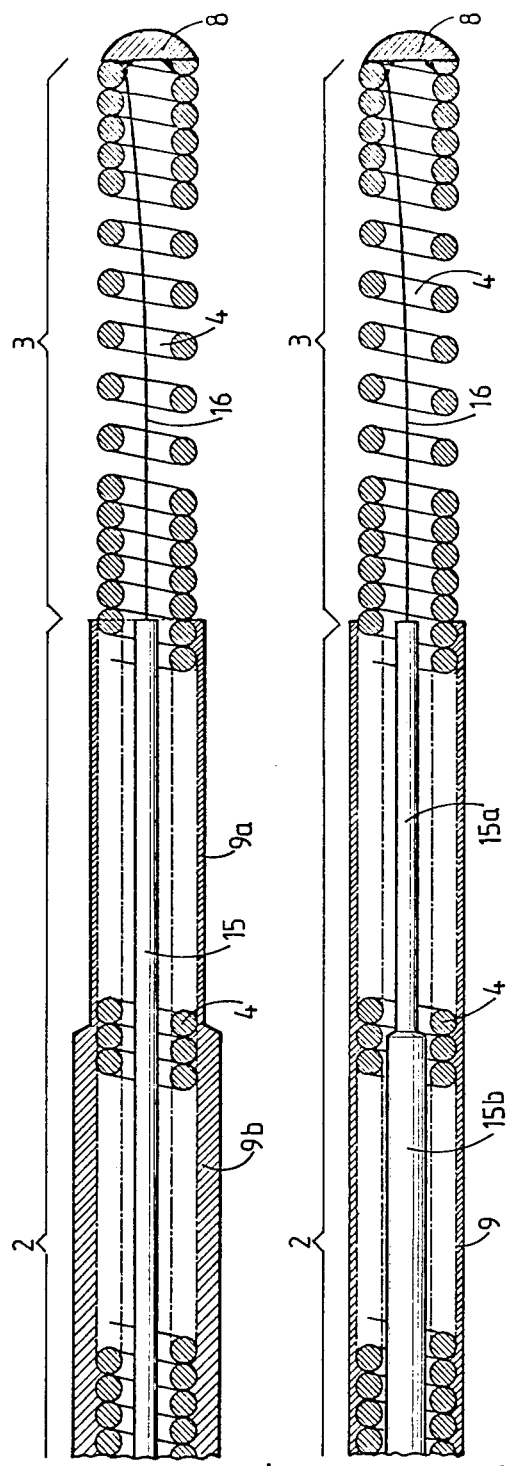
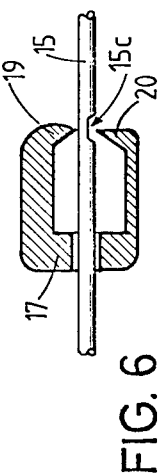
FIG. 3  FIG. 4  FIG. 5  FIG. 6

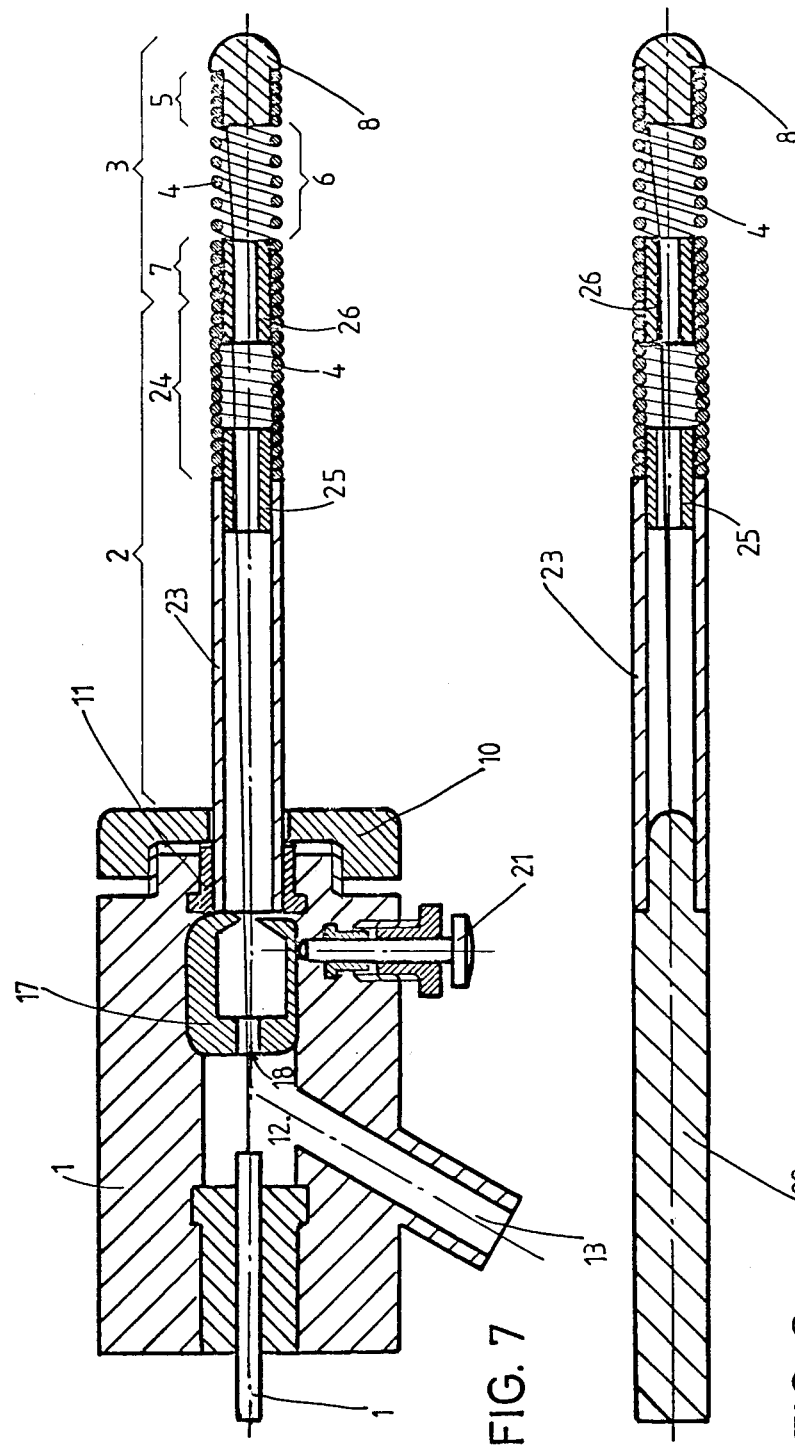

GUIDE FOR A CATHETER

The present invention has for its object a guide for a catheter having a remote control mainly intended for healing cardio-vascular diseases.

One knows from the EP Pat. No. 86115566.1 (not yet published) a guide for a catheter comprising a head formed of a coil spring having abutting coils at both its ends and spaced coils in its central part one end of which is closed by a button whereas the other end is fastened on a stud which is, itself fastened on the end of a thin and flexible tube.

The other end of this thin and flexible tube is connected in a removable way to a control housing. A traction wire fixed in an excentered manner to the button of the head crosses it as well as the thin and flexible tube and is fixed to a traction member of the control housing. Thus by more or less strong tractions on this wire, one can give to the head of the guide of the catheter a more or less accentuated bending. The control housing comprises further means permitting to cut the traction wire once the catheter guide is set in place and before separating this control housing from the thin and flexible tube. Finally this control housing comprises further means permitting to introduce into the thin and flexible tube a contrast liquid which can escape in a blood vessel between the spaced coils of the coil spring of the head of the catheter guide.

Such a catheter guide is generally of very small diameter, less than that of a classical catheter and can therefore be easier inserted into a blood vessel of a patient until its head reaches a stenosis to be healed. When this operation is realized, the control housing is separated from the thin and flexible tube and a full extension is connected to the free end of this tube. This catheter guide constitutes from this instant a guiding means for a tubular catheter which is slid over the catheter guide and which can thus, despite its greater diameter, be easily set in place for the treatment of the stenosis itself.

Such catheter guides are however not entirely satisfactory, practice has in fact shown that if one could easily curve the head thanks to the traction device it was not always possible to cause its straightening, the resilient return force of the spring being too low. Another drawback of these catheter guides resides in the fact that despite its small diameter the tube connecting the head to the control housing is not sufficiently flexible.

Finally a further drawback of these catheter guides resides in the fact that the head is mechanically fixed on the tube and that it is not possible to guarantee absolutely that during the removal of the catheter guide a separation from the head does not occur which then necessitates a surgical intervention.

The present invention has for its object a catheter guide of the type of the one described in application EP-86115666.1 which does not present its drawbacks and which permits further to limit the risks of injury to the blood vessels in which it is introduced and to obtain flexibilities of different values according to the considered portions of the part of the catheter guide connecting the head to the control housing.

The attached drawing show schematically and by way of example several embodiments of the catheter guide according to the present invention.

FIG. 1 is a partial longitudinal cross section of a catheter guide according to the invention the control housing being in coupled position.

FIG. 2 is a partial longitudinal cross section thereof, the control housing being removed and replaced by an extension.

FIG. 3 is a view on a larger scale of the head of the catheter guide and of a part of its tubular member connecting this head to the housing, respectively the extension.

FIGS. 4 and 5 are views on larger scales of variants of execution of the catheter guide.

FIG. 6 shows in cross section a detail of the cutting member of the catheter guide.

FIGS. 7 and 8 show in cross section a variant of the catheter guide, the tubular member being connected to the control housing respectively to the extension.

The embodiment of the catheter guide shown in FIGS. 1 to 3 comprises a control housing 1 connected in a removable manner to the end of a tubular element 2 which is flexible and has a small diameter intended to be introduced all or in part into the blood vessel network of a patient, the other end of which is provided with an orientable head 3.

This orientable head 3 or antenna is realized by a portion of coil spring 4 presenting three distinct zones, a first end zone 5 where the coils of the spring 4 abut, a central zone 6 where the coils of said spring 4 are spaced apart, thereby providing direct communication between the outside of the spring 4 and its central tubular space, and finally, a third zone 7 where the coils of this spring 4 again abut. The terminal zone 5 and the third zone 7 of this head 3 define thus a closed tubular element, which can even be at least partially fluid tight.

The terminal zone 5 of this head is closed by a piece or button 8 welded on the last coil of the spring 4.

The dimensions of this head 3 are important for its use, and so its length is generally comprised between 5 and 20 millimeters whereas its outside diameter is comprised between 0.2 and 0.5 millimeters, preferably about 0.4 millimeter. The diameter of the wire of which the coil is realized is of the order of 0.1 millimeter so that the central tubular space of this head is generally of the order of 0.1 to 0.3 millimeter, preferably about 0.2 millimeter.

This head 3 presents thus on the one hand a central zone 6 permitting as will be seen later on, the passage of a fluid from the tubular internal space of the coil 4 towards the outside of the head and thus into a blood vessel, and on the other hand an important flexibility, particularly due to its central zone 6 having spaced coils which make it easily orientable as will be seen later on.

This head is fixed by the end of its third zone 7 on a tubular element 2 also constituted by a coil spring having abutting coils, preferably made by the continuation of the same spring 4 as the one constituting the head 3.

The length of this tubular element 2 is of about 1 meter and the outside diameter of the spring which constitutes it is of the same order as that of the head, but generally slightly less by 0.05 to 0.1 millimeter. In fact, this tubular element 2 comprises an outside coating 9 of plastic material of a thickness which can vary between a few microns and 0.3 millimeter. This outside coating 9 is obtained by deposition in gaseous phase of the plastic material onto the spring 4 and renders this tubular element completely fluid tight and smooth.

Further-more, this tubular element 3 is able to be bent and to be straightened easily due to its construction which gives it a great smoothness and a great flexibility.

These qualities make it easier for the practitioner to have the catheter guide penetrate into a blood vessel of the patient, its surface being smooth and its flexible ability being great, so that the risks of causing damage to these blood vessels are greatly reduced.

The free end of this tubular element 2 is fastened in a removable but fluid tight way to the control housing 1, in the example shown through a screw and nut coupling 10 comprising a joint or stuffing box 11. The inside cavity 12 of this housing 1 communicates with the central tubular space of the element 2 and of the head 3 and can be fed with a contrast liquid for example by means of a conduit 13.

The control housing comprises further a control member 14, sliding axialy in this housing in a fluid tight manner, connected by a traction member 15 to an excentered point of the free end of the head 3 of the catheter guide. This traction member 15 extends within the housing 1, within the tubular element 2 and the head 3. It has a very thin and supple portion 16, of a diameter of the order of 1 to 5 hundredths of 9 millimeter extending the length of the head 3 and a portion 15 which is thicker and more rigid connecting this portion 16 to the control member, having a diameter of 1 to 2 tenths of a millimeter.

Thus, the operator when pulling axially on the control member 14 can cause a curvature of the head 3, the bending of which is not influenced or rendered difficult through the traction member 15,16 since in this zone it is very supple and flexible.

When the operator wants to straighten the head 3, if it doesn't suffice to stop pulling on the control member 14, the friction force between the traction member 15 and the tubular element 2 being so high that the elasticity of the spring of the head permits such a straightening, the operator pushes the control member 14 toward the housing causing a displacement of the portion of great diameter 15 of the traction member into the tubular element 2 against the friction force. The elasticity of the head 3 has then only to straighten the thin and very flexible portion 16 of this traction member which imposes practically no resistance to be acted against.

Thanks to these two new and original characteristics, tubular element 2 realized with a coil spring covered with a layer of plastic material and traction member 15 which is very supple at its end and more rigid along the rest of its length, the present catheter guide remedies the drawbacks of the similar known devices and permits achieving the objects of the invention.

As in the existing catheter guide, the control housing 1 comprises also a cutter constituted by a knife 17, housed in the housing 1 comprising a bore 18 giving passage to the traction member 15 and two jaws one 19 fixed and the other 20 displaceable against its own elasticity and a push member 21 which is accessible from the outside of the housing.

Thanks to this cutter, the operator may, when the catheter guide is introduced in service position in the blood vessel of the patient, cut the traction member, which permits thereafter disconnecting the housing 1 from the tubular element 2 and to fitting at the end of it a plain handle or extension 22 as shown at FIG. 2. This handle 22 presents an outside diameter practically equal that one of the tubular element 2.

In variant, the fore part of the tubular element 2 can be provided in a known manner with an expansible balloon which can be fed by liquid from an annular conduit surrounding the coating 9 and connected in the control housing 1 to a particular feeding duct.

According to the desired uses, it is often desirable that the tubular element can present different degrees of flexibility, more rigid in the vicinity of the control housing 1 and more flexible in the vicinity of the head 3.

This can be achieved as in the variant shown in FIG. 4 by a coating or sleeve of variable thickness. The frontal part of the tubular element receives a thin coating 9a whereas the rear part of this element 2 is provided with a coating 9b which is thicker, thus increasing the rigidity of this element 2.

According to the desired flexibility characteristics of the tubular element 2 several thickness differences (3 to 5) of this coating 9 can be provided. It is also possible by this means to give to this tubular element a greater rigidity in its central portions than in its fore or rear portions.

In another variant shown in FIG. 5 one obtains these differences in flexibility of the tubular element 2 through different diameters of the traction member, the portion of it extending within the tubular element 2 having portions 15a, 15b of different diameters. The greater the cross section of the traction member, the greater is its rigidity.

In certain cases where the diameter of the traction member in the vicinity of the cutter would be too great to permit an easy cutting of it, one can, as shown in FIG. 6 provide for a local reduction 15c of the section of this traction member 15 or a smaller diameter at this location.

The main advantages obtained by the catheter guide of the present invention are:
1. the whole instrument is more supple and flexible
2. it is easier or even possible to straighten the head of the instrument after it has been bent
3. injuries to the walls of the blood vessels are avoided
4. it is possible to penetrate arterial networks of small calibre and having many turns.

The second embodiment shown in FIGS. 7 and 8 comprises a tubular member 2 connecting the head 3 to the control housing 1 respectively to the extension 22 which comprises a first portion 23, connected through one end to the control housing and formed by a thin and flexible tube; and a second part 24 connected to the head 3 constituted by a coil spring having abutting coils covered by a plastic envelope the base of which is fixed onto a bored stud 25 itself fitted in the inside of the tube 23 and the other end of which is fitted onto a hollow stud 26 fitted inside the head 3.

One obtains thanks to this realization a tubular member having a more supple end.

We claim:

1. In a catheter guide comprising a head formed by a coil spring having a central zone wherein the coils are spaced apart and two zones on opposite sides of said central zone wherein the coils of the spring abut each other, said head having a closed free end and a tubular element connecting said head to a control housing to which said head is removably secured, a control device for bending the head comprising a control member sliding in the housing and connected to a traction member passing through said housing and through the tubular element and the coil spring and eccentrically connected to said free end, and a cutter for the traction member carried by said control housing; the improvement in which the tubular member is comprised along at least a portion of its length by a coil spring having abutting coils covered by a fluid tight coating of plastic material.

2. A catheter guide according to claim 1, in which the coil spring forming the head and the tubular member are the same spring.

3. A catheter guide according to claim 1, in which said traction member has a smaller cross section adjacent said free end than adjacent said control housing.

4. A catheter guide according to claim 3, in which said traction member is a metal wire and said portion of the traction member adjacent said free end is from 1 to 5 hundredths of a millimeter in diameter.

5. A catheter guide according to claim 1, in which said cutter has opposed jaws on opposite sides of said traction member, said traction member having a reduced thickness between said jaws to facilitate cutting of the traction member.

6. A catheter guide as claimed in claim 1, in which said coating of plastic material of the tubular element has a constant thickness throughout its length.

7. A catheter guide according to claim 1, in which said coating of plastic material of the tubular element has several different thicknesses throughout its length decreasing from said housing toward said free end.

8. A catheter guide according to claim 1, in which said tubular member throughout its length is constituted by a coil spring having abutting coils.

9. A catheter guide according to claim 1, in which only a portion of said tubular element nearest said head is formed by a coil spring having abutting coils.

* * * * *